United States Patent [19]

Nestor et al.

[11] Patent Number: 4,768,953
[45] Date of Patent: Sep. 6, 1988

[54] GOLDEN LINK CALIPER INSTRUMENT

[76] Inventors: Jack Nestor, 110 1st Ter., San Marino Is., Miami Beach, Fla. 33139; William A. Shoemaker, Jr., 6860 SW. 96th St., Miami, Fla. 33156

[21] Appl. No.: 877,237

[22] Filed: Jun. 23, 1986

[51] Int. Cl.$^4$ ............................................. A61C 19/04
[52] U.S. Cl. ...................................... 433/72; 33/511; 33/514
[58] Field of Search ................... 433/72; 33/179.5 A, 33/511, 513, 514, 150

[56] References Cited

U.S. PATENT DOCUMENTS

| | | | |
|---|---|---|---|
| 1,133,587 | 3/1915 | Stenersen | 33/150 |
| 1,246,408 | 11/1917 | Fish | 433/72 |
| 1,321,924 | 11/1919 | Kuldell | 33/150 |
| 3,906,634 | 9/1975 | Aspel | 433/72 |
| 4,416,063 | 11/1983 | Nestor et al. | 33/163 |

Primary Examiner—Robert Peshock
Assistant Examiner—Adriene J. Lepiane
Attorney, Agent, or Firm—Erwin M. Barnett

[57] ABSTRACT

An instrument particularly adapted for use in dentistry but capable of a wide variety of other applications and including a divider-caliper type instrument typically having two members of equal length and substantially corresponding configuration pivotally secured to one another wherein opposite ends of each member is defined by different sized points. A scale format is formed on an exposed surface on at least one of the members and is based on the golden proportion of 1 to 0.618. Accordingly, a plurality of scale settings are disposed in predetermined spaced apart relation to one another based upon formulized calculations resulting in use of the caliper instrument in dental applications including direct oral procedures, dental laboratory techniques, cephalometric analyses as well as aiding in the establishment of arch form, tooth size and outline form as well as cusp-fossa proportions and the accurate and simple placement of developmental grooves.

4 Claims, 1 Drawing Sheet

U.S. Patent
Sep. 6, 1988
4,768,953
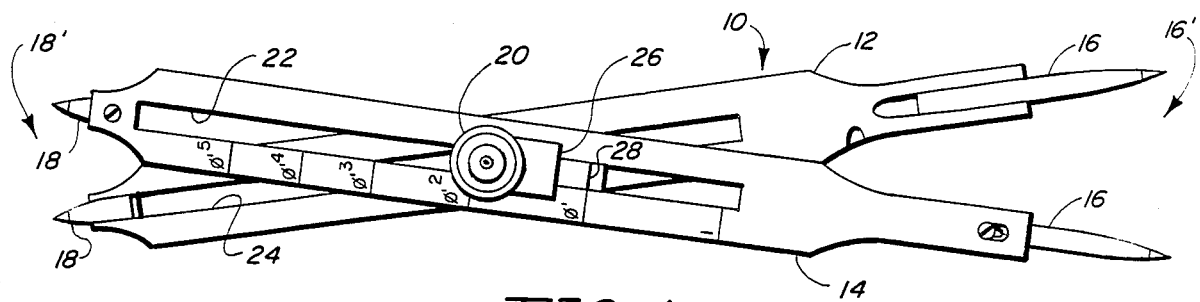
FIG. 1
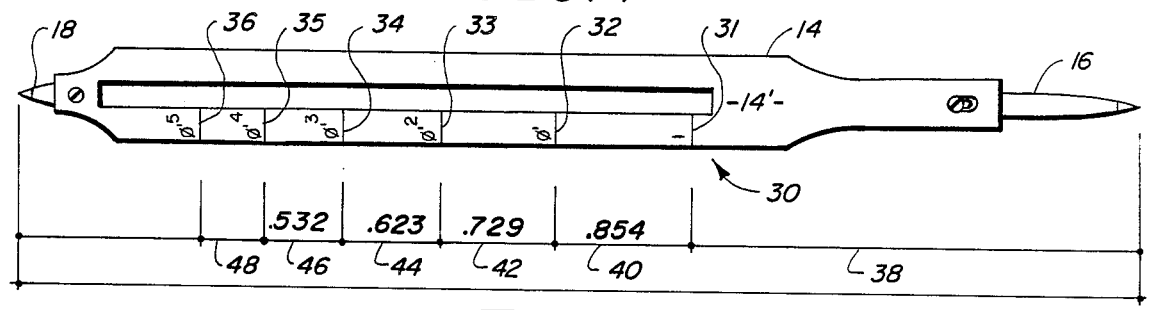
FIG. 2
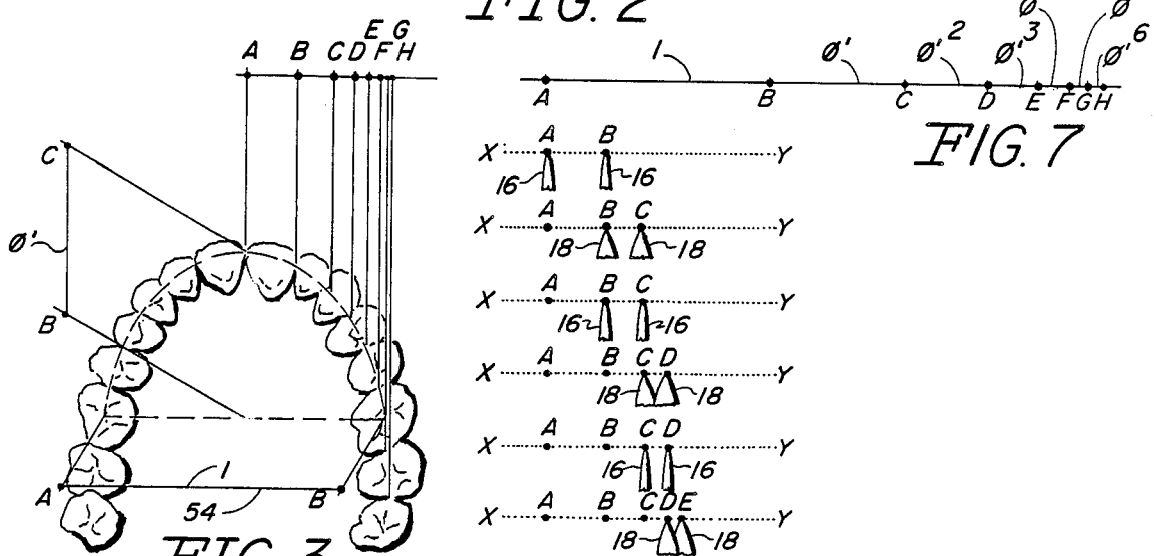
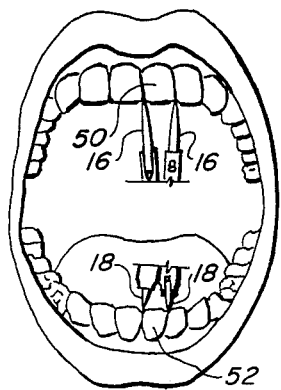
FIG. 3
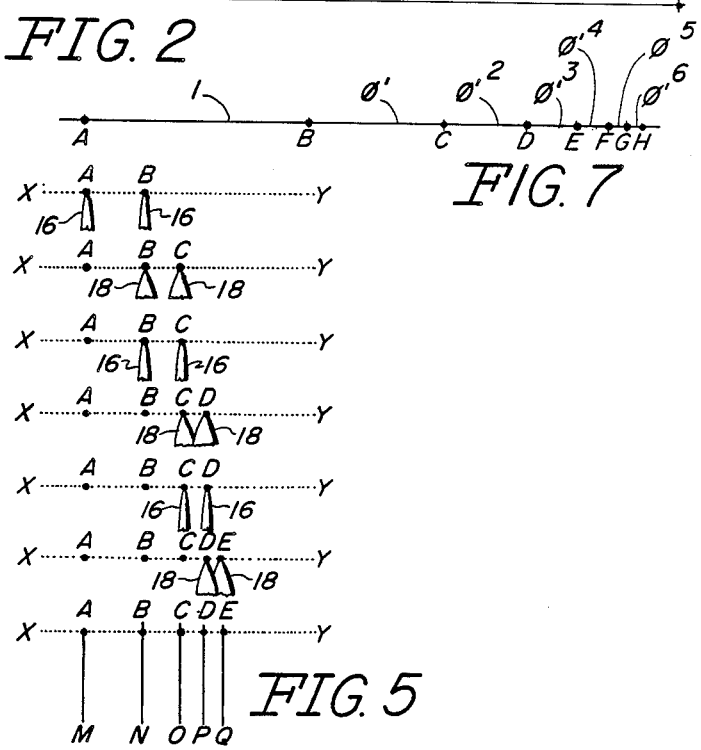
FIG. 4
FIG. 6

GOLDEN LINK CALIPER INSTRUMENT

BACKGROUND OF THE INVENTION

1. Field of the Invention

This invention relates to divider-caliper type instrumentation specifically scaled to include a plurality of scale settings disposed along the scale length and based on the golden proportion of 1 to 0.618 wherein the instrument is particularly adapted for utilization in a wide variety of dental procedures as well as other diverse applications.

2. Description of the Prior Art

The "golden proportion" is a well recognized mathematical phenomena occurring in nature in both form and function and, has been acknowledged to be present in physiology as well as forming the basis of aesthetic sense of human anatomy. Accordingly, the golden proportion, if embodied in specific instrumentation can be useful to such technichal and scientific fields as dentistry, medicine as well as other diverse fields including the graphic arts. A book entitled "THE DEVINE PROPORTION A Study In Mathematical Beauty" by H. E. Huntley, published by Dover Publications, Inc. is one of many publications on the subject of the "golden proportion" and discusses many of the fascinating aspects thereof.

Also, U.S. Pat. No. 4,416,063 to Jack Nestor and William A. Shoemaker, Jr. (present applicant) is directed towards instrumentation in the form of golden proportion calipers wherein a reference index located between a pair of variable indices and a sectionalized threaded spindle having opposite end sections with reverse threads of different pitches in a ratio of approximately 1 to 0.618. Each spindle section threadingly engages a support for one of the variable indices whereby rotation of the spindle simultaneously adjusts the ditances between each variable index and the reference, the distances being maintained in the aforementioned ratio known as the "golden proportion."

While the structures of the type disclosed in the above noted patent as well as the various publications pertinent to this subject are certainly operable for their intended function, there is still a need for a more precise instrumentation which, as set forth hereinafter, may be more specifically embodied in the form of a divider-caliper capable of performing numerous functions and procedures specifically beneficial to the medical fields, especially dentistry, but of course applicable to a wide variety of other areas.

SUMMARY OF THE INVENTION

The subject of the present invention is generally a divider-caliper instrument typically formed of two pivotally attached members of equal length and substantially corresponding configuration each having opposite ends respectively defined by a long point and a snub point. The members are pivotally connected to one another by a set screw movable along the length of each of the members and which defines a pivotal axis for relative movement between the members. When assembled in pivotal interconnection with one another, the resulting caliper comprises one long points end defined by the relatively positionable long points of each member and correspondingly the opposite snub points ends defind by the relatively positionable snub ends of each member.

An important feature of the present invention is the provision of a scale on an exposed surface on at least one of the members wherein the scale comprises a plurality of scale settings each disposed in a predetermined spaced apart relation to one another. More particularly, the scale and the placement of each of the scale settings relative to one another is based on the aforementioned "golden proportion" of 1 to 0.618.

A first scale setting of the plurality of scale settings may be represented as 1 and primarily serves as a reference setting as well as being representative of the midpoint of the length of the instrument. However, it should be noted that depending upon the particular structure of the instrument and particularly an alignment marker connected to and movable with the set screw, the first scale setting or reference scale setting, which may be designated as "1" is offset to compensate for the outward projection of the alignment marker. Accordingly, when the "hair line" on the alignment marker is in perfect alignment with the first scale setting or reference scale "1", then the set screw and accordingly, the defined pivotal axis is set at the exact midpoint of the instrument. The results would be that the spacing between the long point end and the snub point end would be in a ratio of 1 to 1.

With the provision of the subject unique scale on the divider-caliper type instrument, it may be used for the following determinations, by way of example:

1. Establishment of the width of the maxillary central incisors by cross-reference with mandibular incisors.
2. Establishment of many types of Golden Grids from which tooth arrangement can be most aesthetically positioned.
3. Establishment of arch form, in most cases, with extreme precision.
4. Establishment of gingival incisal tooth height.
5. Formation of developmental lobes (labial anatomy) in anterior teeth.
6. Determination of the location and length of cracks and the individualized staining in anterior teeth.
7. Establishment of occlusal table width.
8. Establishment of mesial-distal width of all teeth.
9. Location of cusp and groove.
10. Pit location.
11. Determination of cusp height, as in a mandibular first bicuspid.
12. Use in comparative cephalometric analyses.
13. Location of vertical positon of both maxillary and mandibular central incisors.

It should be emphasized at this point that the determinations set forth above are representative only of the possible uses of the subject instrumentation of the present invention and are provided by way of example and not to limit the scope of the use of the subject instrument.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a front plan view of the golden link calipers of the present invention.

FIG. 2 is a front plan view of one member of the calipers wherein a scale is formed along the length of an exposed surface thereof wherein specific relative distances are set forth in schematic form.

FIG. 3 is a schematic representation of a dental arch representing a steady model of a prosthesis generally representative of an ideal arch form.

FIG. 4 is a frontal view of the representation of the instrument, represented in partial cutaway form, being applied to the measurement of specific teeth therein.

FIG. 5 is a schematic representation of the formation of a grid.

FIG. 6 is a front view with a perspective reference grid being formed on a sheet of paper or like matter.

FIG. 7 is a schematic representation of proportional distances in another embodiment of a grid formation.

Like reference numerals refer to like parts throughout the several views of the drawings.

DETAILED DESCRIPTION OF THE PREFERRED EMBODIMENT

As shown in FIG. 1, the divider-caliper instrument based on the golden proportion is generally indicated as 10 and includes correspondingly configured and equally dimensioned members 12 and 14. Each member 12 and 14 includes a long point end 16 and a snub point end 18 wherein the assembled instrument as shown in FIG. 1 comprises a long point end generally indicated as 16' and a snub point end generally indicated as 18'. The instrument 10 further includes a set screw 20 passing through the elongated slots 24 and 22 in members 12 and 14, respectively, and structured to travel along the length thereof. The set screw 20 is of course structured to define a pivotal axis or axis of movement of the members 12 and 14 as they are moved out of an aligned, parallel relation to one another (not shown) to a separated or divider measuring position as represented in FIG. 1.

Further, the instrument 10 includes an alignment marker 26 having a hairline or like indicator 28 thereon. The hairline 28 is designed to be aligned with any one of a plurality of scale settings of the scale generally indicated as 30 extending along the length of one exposed face of at least one of the members 12 and 14 (see FIG. 2). The scale and the provided disposition of the scale setting as represented by reference numerals 31 through 36, is of great importance to the present invention and will be described in greater detail hereinafter. However, the alignment of the "hairline" 28 of the alignment marker 26 with any one of a plurality of scale settings 31 through 36 in turn determines the placement of the set screw 20 and thereby the placement or location of the pivotal axis defined by the set screw 20 of the members 12 and 14 as they move relative to one another.

An important feature of the present invention is the scale generally indicated as 30 and more particularly the fact that the scale is based on the golden proportion 1 to 0.618. Accordingly, the scale 30 comprises a plurality of scale settings 31 through 36 formed on an exposed face 14'0 of at least one of the members 12 and 14. It should be noted that the number of scale settings 31 through 36 may vary depending upon the length of the instrument and/or its intended use and application. However, the location of each of the scale settings is specifically determined and based, as set forth above, on the aforementioned and explained "golden proportion."

A first of the plurality of settings is indicated as 31, by reference numeral, and appears on the exposed face 14' by a preferred indication as "1". This first scale setting 31 is specifically located along the length of the member 14 so as to indicate or more specifically locate the pivotal axis defined by set screw 20 at the exact midpoint of the instrument. Accordingly, the distance 38 indicated by the schematic distance scale representation in FIG. 2 is the distance from the long point end 16 of the member 14 sufficient to place the first scale setting 31 at a permanent and predetermined location. This predetermined location is defined by and dependent on the length and/or configuration of the alignment marker 26 such that when hairline 28 is aligned with first scale setting 31, the pivotal axis defined by set screw 20 will be in the true midpoint location between ends 16 and 18 of the member 14 and more specifically, define the pivotal axis between members 12 and 14, when assembled. When so positioned, the space between each of the long points 16, 16 and each of the snub points 18, 18 will be in a ratio of 1 to 1.

Based on the above, the specific placement of each of the successive settings 32 through 36 is determined by mathematical analysis of the golden proportion. Specifically, the second scale setting 32 is disposed a specific distance from the first scale setting 31 indicated on surface 14' as "1". Further, the first scale setting 31 may be considered a reference scale setting in that the distance 38 (see FIG. 2) is determined by proper placement of the first scale setting 31 in order to locate the pivotal axis defined by set screw 20 (FIG. 1) at the exact midpoint between the ends of the instrument 10 when the hairline 28 of alignment marker 26 is aligned with the first setting 31.

The formula:

$$d_s = d_1 - (d_1 \times K)$$

enables the remainder of scale 30, shown in FIG. 2, to be constructed so that, when reference or long point end 16' is set at unity, the snub point end 18' will measure the respective values of the powers of $\phi'$ as follows:

$\phi' = (0.618)^1 = 0.618$, which is the lesser ratio of the golden proportion.

$\phi'^2 = (0.618)^2 = 0.3189$
$\phi'^3 = (0.618)^3 = 0.236$
$\phi'^4 = (0.618)^4 = 0.1459$
$\phi'^5 = (0.618)^5 = 0.090$ In the above formula, $d_s$ = the respective distances between adjacent scale settings when $d_1$ = the distance between the preceding setting (the setting from which $d_s$ is to be measured) and the next preceding setting and $k = \phi'^4 = 0.1459$. To locate scale setting 32 ($\phi'$), although there is no apparent next preceding setting, the formula is applicable and does provide the value for distance 40 when $d_1$ is assigned a value of unity or 1.

Thus, distance $40 = 1 - (1 \times 0.1459) = 0.854$

Further applications of the formula to locate scale settings 33 ($\phi'^2$), 34 ($\phi'^3$) and 35 ($\phi'^4$) by computing distances 42, 44, and 46, respectively, are:

Distance $42 = 0.854 - (0.854 \times 0.1459) = 0.729$
Distance $44 = 0.729 - (0.729 \times 0.1459) = 0.623$
Distance $46 = 0.623 - (0.623 \times 0.1459) = 0.532$ Distances 40, 42, 44, 46 and 48, indicated along scale 30 shown in FIG. 2, are in inches and differ in value from the ratios resulting in measurements made by instrument 10.

As an example of specific practical application of the subject instrument 10 but again, by way of example only, a golden grid or frontal grid of prosthesis may be calculated and derived at in the following manner. As the frontal view is most apparent in a smile, a frontal grid based upon the apparent dimensions of the upper teeth can be a useful tool for aesthetic comparisons, the most popular fittings conform with a primary "golden" relationship and while the spacing of the existing teeth and individual taste may modify the prosthesis, the grid is an excellent reference to note where modifications occur.

The subject instrument 10 is as valuable in direct oral procedures as it is in the dental laboratory as set forth above. In order to form the aforementioned frontal grid where the width of the central incisor is known or can be determined using the subject instrument, the process of forming the subject frontal grid is as follows: On a sheet of paper or any applicable medium, a straight line XY (see FIG. 5) is drawn. The length of the line should be at least 10 centimeters. Set the subject caliper instrument 10 at the $\phi'$ setting. Spread the long ended points 16 of the instrument 10 to precisely measure the width of the central incisor 50 (see FIG. 4) at its greatest mesial-distal width. Next, do not change the spread on the instrument 10. Place both long end points 16 on line XY and properly locate points A, B (see FIG. 5). Next, do not change the spread on the instrument 10 and place the opposite snub ended points 18 of the instrument 10 on line XY by placing one point in mark B and the other point on the opposite side of mark B to form point C.

Change the spread on the instrument 10 by placing the long ended points 16 of the instrument 10 on marks B and C of line XY. Next, do not change the spread of the instrument 10 but place the opposite snub ended points 18 of the instrument 10 on line XY by placing one point on mark C and forming the other point D on the same line XY oppositely disposed from the point B relative to point C.

Change the spread on the instrument 10 by placing the long ended point 16 of the instrument 10 on marks C and D. Next, do not change the spread on the instrument 10 but place opposite snub ended points 18 of the instrument 10 on line XY by placing one point in the mark D, place the other point on opposite side from points A, B and C and thereby forming the new mark E on the line.

The arrangement and accuracy of the distance between the points A,B,C,D, and E can be readily checked by adjusting the caliper screw setting and mark alignment such that hairline 28 is in alignment with the fourth scale setting 34 or the scale indication $\phi'^3$. Next, use the elongated point 16 to measure from mark A to B, do not change the spread on the caliper but use the opposite snub ended points 18 to check the distance from mark D to E. The spread of the snub ended points 18 should be equal to the space between marks D and E.

Now draw parallel lines (see FIG. 6) AM, BN, CO, DP, and EQ to the extent that each line should be drawn perpendicular to line XY. Obviously if desired, more lines can be drawn using the pattern developed further, in the manner set forth above.

The frontal grid or golden link grid formed by the instrument 10 of the present invention is now ready for use. The grid thus formed measures apparent (not actual) widths of the teeth in the upper jaw as seen from the frontal view (see FIG. 6) by placing the prosthesis of the grid, it is possible to make a comparison based on the aesthetic proportions. The grid should be flat, with line AM being the midline.

Because of the marked curvature of most arches, it will be found to be effective to use a half grid at a time rotating it to conform with the arch curvature. When rotating, key in line BN to the junction of the central incisor and lateral incisor. AM will run wide of the middle line but the other lines of the grid should conform to the teeth width. For the other side of the upper jaw, simply turn the grid upside down and repeat. Obviously, it should be apparent at this point that there are many variations to the frontal grid. However, it can be easily mastered as a basic construction however, before proceeding to other forms.

With reference to FIGS. 3, 4 and 7, a frontal grid may be created where the width of the central incisor is not known. To accomplish this, adjust the calipers 10 to the $\phi'$ setting. Using the small snub ended points 18 of the calipers, measure the width of the lower central incisor 52. Next, do not change the spread on the instrument 10 but place the opposite long ended point 16 of the instrument 10 to measure the likely width of the upper central incisor. Once the width of the upper central incisor is found proceed with the creation of the frontal grid as outlined above.

Next with regard to FIGS. 3 and 7, the arch illustrated in FIG. 3 closely follows several study models which have been termed as being close to an ideal arch form. Virtually all of the dimensions of harmonious and functional import can be determined through use of the subject instrument. In performance, set the instrument to the $\phi'$ setting. Next, using the long ended point of the instrument 10 to measure the distance from the central fossa to central fossa (line 54 of FIG. 3) indicated by reference "1" of first molars. Next, follow successively the steps as set forth above to create the line represented in FIG. 7 for reference measurement of the relationship such that each successive distance is one higher power of $\phi'$ that is, CD is equal to $\phi'^2$, DE being equal to $\phi'^3$, etc. Based on the formation of the line segment and designated distances in FIG. 7, the following relationships have held true, again when referring to the line and designated segments in FIG. 7.

1. Central fosa to central fossa of first molars = 1.00 (segment AB)
2. Distal fossa to distal fossa of second bicuspids = $1.00 - \phi'^6$ (segments AB−GH)
3. Mesial fossa to mesial fossa of second bicuspids = $1.300 - \phi'^5$ (segments AB−FG)
4. Distal fossa to distal fossa of first bicuspids = $1.00 - \phi'^4$ (segments AB−EF)
5. Mesial fossa to mesial fossa of first bicuspids = $1.00 - \phi'^3$ (segments AB−DE)
6. Mesial of the cuspid to mesial of the cuspid = $\phi'$ (segments BC)
7. Mesial of the lateral to mesial of the other lateral = $\phi'^2$ (segments CD)
8. Mesial distal length and labial lingual width of the first molars = $\phi'^3$ (segments DE)
9. Mesial distal width of the lateral incisors = $\phi'^4$ (segments EF)
10. Central fossa to central fossa of second molars = $1.00 + \phi'^3$ (segments AB+DE)
11. Central fossa to central fossa of third molars = $1.00 + \phi'^5$ (segments AB+FG)
12. Buccal surface to buccal surface of first molars = $1.00 + \phi'^4 + \phi'^5 + \phi'^6$.
(If this value is reassigned a new value of 1.00 then buccal surface of cuspid to cuspid now becomes $\phi'$).

The divider type caliper instrument herein disolosed is seen to achieve the several objects of the invention and to be well adapted to meet conditions of practical use. As various possible embodiments might be made of this invention, and as various changes might be made in the disclosed instrument, it is to be understood that all matters herein set forth or shown in the accompanying drawing are to be interpreted as illustrative and not in a limiting sense.

What is claimed is:

1. A divider type caliper instrument having two caliper members of equal length, each having a first end distinguishable from a second opposite end, and an adjustable pivotal interconnection between said members, comprising:
    (a) a scale formed on and extending longitudinally along an exposed surface of at least one of said members,
    (b) said scale having a plurality of settings, for said pivotal interconnection for successive powers of phi' whereby said second opposite ends of the caliper members determine the value of the respective phi' setting, when said first member ends measure unity as a reference, where phi'=0.618,
    (c) a first of said settings being phi' located at a distance of 0.854 units in the direction of said second end measured from the midpoint of the caliper members,
    (d) said distance of 0.854 units being derived from the formula:

$$d_s = d_1 - (d_1 \times phi'^4)$$

wherein $d_1$ is given a value of 1,
    (e) each setting for said successive powers of phi' progressing toward said caliper member second opposite ends being derived from said formula wherein $d_s$ is the distance between a previously determined setting and the setting to be derived and $d_1$ is the distance between said previously determined setting and the next preceding setting.

2. The instrument defined in claim 1 in which said midpoint is included as a functional setting.

3. A divider type caliper instrument having two caliper members of equal length, each having a first end distinguishable from a second opposite end, and an adjustable pivotal interconnection between said members, comprising:
    (a) a scale formed on and extending longitudinally along an exposed surface of at least one of said members,
    (b) said scale having a plurality of settings for said pivotal interconnection for successive powers of phi' whereby said second opposite ends of the caliper members determine the value of the respective phi' setting when said first member ends measure unity as a reference, where phi'=0.618,
    (c) a first of said settings being phi' located at a distance of 0.854 units in the direction of said second end measured from the midpoint of the caliper members,
    (d) a second successive scale setting of said plurality of settings being phi'^2 located at a distance of 0.729 units from said phi' setting, and
    (e) a third successive scale setting of said plurality of settings being phi'^3 located at a distance of 0.623 units from said phi'^2 setting.

4. The instrument defined in claim 3 in which a fourth successive scale setting of said plurality of settings is phi'^4 located at a distance of 0.532 units from said phi'^3 setting.

* * * * *